(12) United States Patent
Pfeiffer et al.

(10) Patent No.: US 6,885,464 B1
(45) Date of Patent: Apr. 26, 2005

(54) 3-D CAMERA FOR RECORDING SURFACE STRUCTURES, IN PARTICULAR FOR DENTAL PURPOSES

(75) Inventors: Joachim Pfeiffer, Bensheim (DE); Axel Schwotzer, Gross-Gerau (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 09/342,736

(22) Filed: Jun. 29, 1999

(30) Foreign Application Priority Data

Jun. 30, 1998 (DE) ........................................ 198 29 278

(51) Int. Cl.[7] .............................................. G01B 11/24
(52) U.S. Cl. .......................... 356/602; 356/603; 433/29
(58) Field of Search ................................ 356/601–607, 356/614, 615, 622, 623; 250/559.21, 559.22, 559.24; 433/2, 4, 24, 29, 44, 68, 223; 600/476, 473, 478

(56) References Cited

U.S. PATENT DOCUMENTS

| | | | |
|---|---|---|---|
| 4,184,175 A | * | 1/1980 | Mullane, Jr. ................. 348/66 |
| 4,575,805 A | | 3/1986 | Moermann et al. ......... 364/474 |
| 4,837,732 A | | 6/1989 | Brandestini et al. ... 364/413.28 |
| 5,424,836 A | | 6/1995 | Weise et al. |
| 6,086,366 A | * | 7/2000 | Mueller et al. ............... 433/29 |
| 6,263,234 B1 | * | 7/2001 | Engelhardt et al. ......... 600/476 |
| 6,614,538 B1 | * | 9/2003 | Basler et al. ............... 356/602 |

FOREIGN PATENT DOCUMENTS

| | | |
|---|---|---|
| DE | 3810455 | 10/1989 |
| DE | 9013454 | 1/1992 |
| DE | 90 13 454.0 | 2/1992 |
| DE | 4034007 A1 * | 4/1992 |
| DE | 4218219 | 12/1993 |
| EP | 0 250 993 | 1/1988 |
| EP | 0968687 A2 | 1/2000 |
| WO | WO 98/11403 | 3/1998 |

OTHER PUBLICATIONS

Pfeiffer, J., et al., "Dreidimensionale Optische Vermessung von Zähnen," Technisches Messen: Sensoren, Geräte, Systeme [Meterology: Sensors, Devices, Systems], pp. 254–261 (Jun. 1996).

* cited by examiner

Primary Examiner—Hoa Q. Pham
(74) Attorney, Agent, or Firm—Foley & Lardner LLP

(57) ABSTRACT

A 3-D camera and a method for recording surface structures on an object of interest by triangulation, in particular for dental purposes. The camera provides for producing a group of light beams in order to illuminate the object of interest via a projection optical path, an image sensor for receiving light back-scattered by the object of interest via an observation optical path, and provides, in the projection optical path, for producing a pattern projected onto the object of interest. To avoid ambiguities in the event of large height differences, the camera provides for the projection optical path and/or the observation optical path for altering the triangulation angle, which is defined by the angle between the centroid beam of the projection optical path and the centroid beam of the observation optical path. The proposed process involves the taking of at least two 3-D measurements of the same object of interest with different triangulation angles.

25 Claims, 1 Drawing Sheet

3-D CAMERA FOR RECORDING SURFACE STRUCTURES, IN PARTICULAR FOR DENTAL PURPOSES

BACKGROUND OF THE INVENTION

1. Field of the Invention

The invention relates to a 3-D camera for recording surface structures on an object of interest by means of triangulation, in particular for dental purposes.

2. Relevant Prior Art

3-D cameras (i.e., cameras for recording three-dimensional structures) for dental applications mostly serve the purpose of recording the surface structure of a tooth in the mouth of a patient. Therefore, they must fulfil several requirements such as the possibility of using the camera "endoscopically" in the mouth of the patient, the possibility of placing the camera in the mouth manually, and a measuring time short enough to avoid blurring even if the camera is used without further fixation. It should further be possible to record the complete surface structure if possible in a single exposure, at a maximum in two exposures. It is therefore important that the results of the measurement are displayed to the operator as shortly as possible after the exposure in order to give him the opportunity to repeat the exposure if necessary. From the resulting 3-D contour data of the surface structure a dental implant will be constructed and produced. The necessary precision of the measurement therefore corresponds to the necessary precision of the dental implant. The maximum gap width that may be tolerated in dental applications is about 100 micrometers ($\mu$m). As the steps following the measurement induce further tolerance, a precision of ±25 $\mu$m in the relevant measurement volume appears to be a sensible requirement.

U.S. Pat. No. 4,575,805 discloses a 3-D camera with which a surface structure on an object of interest can be recorded in terms of height or depth differences. This conventional 3-D camera has a projection optical path and an observation optical path, which make an angle with an optical axis of the 3-D camera. A light source for emitting a group of light beams in the direction of an object of interest is arranged in the projection optical path. The light reflected by the object of interest is guided through the observation optical path to an image sensor of the 3-D camera. The signals from the image sensor can be fed to an evaluation unit, so that an image of the surface structure can be created on a display device. This 3-D camera is suitable in particular for recording a cavity of a tooth.

EP-A-0 250 993 also discloses such a 3-D camera. For determining the height or depth differences of the surface structure, means are provided for producing a reference pattern in such a way that the reference pattern can be projected onto the surface structure. With the aid of the light which is reflected by the surface structure and is incident on the image sensor, and in conjunction with evaluation electronics for carrying out a process which is referred to as phase-shifting triangulation and is explained in more detail in the aforementioned document, the surface structure can be assessed in terms of height and depth differences and presented as a pseudo-three-dimensional image on a monitor.

A 3-D camera is also disclosed in the journal "Technisches Messen: Sensoren, Geräte, Systeme" [Metrology: sensors, devices, systems], June 1996, pages 254 to 261, Oldenbourg-Verlag B3020.

Although in principle several different triangulation techniques are known, in each of the above-mentioned documents the measurement itself is performed by phase-shifting triangulation. The basic principles of this technique are well-known from the general literature and are described in part in the mentioned documents. In the following a brief introduction is given.

An object is observed by a camera with a planar detector element, which generates a two-dimensional digital image. The object is thus described by a data set in which discrete intensity values are assigned to discrete pixels in the lateral dimension. In order to generate information about the third dimension (object height z), the object is illuminated with incident light in a structured fashion and observed from a direction different from the direction of the incident light, i.e., under a triangulation angle.

The projection and the observation optics must be arranged in a fixed and known spatial relationship to one another. They may be formed by the same system of lenses which are transmitted in different areas or under different angles. For influencing the beam geometry, an additional field lens may be present close to the object.

The illumination structure is generally periodic in one dimension and homogeneous in the other dimension, i.e., it is a strip pattern (line pattern). For determining the height values of the third dimension, this line pattern is moved across the object, and during this moving operation at least three, mostly four or five images are recorded.

The application of phase-shifting triangulation to recording dental structures is characterized by a number of specific demands. The most important ones are imposed by the size and typical shape of the object and by the necessary precision. For measuring edges with height differences of up to about 10 millimeters (mm) with a precision of 25 $\mu$m in all dimensions, a high lateral resolution of the optical components is necessary. The simultaneous need for a high depth of field imposes demands to the system that are at the edge of what is possible with visible light because of the diffraction limit. A short wavelength would be desirable if suitable light sources were available.

The demand of recording cavities with steep walls on all sides requires a small triangulation angle. The small object size allows to use a telecentric beam path, which leads to simplifications in the evaluation algorithms. A telecentric beam path also is a good compromise with respect to the shape to be measured, as it allows measuring cavities as well as stumps with steep flanges.

There are several techniques by which the actual measurement may be performed with a 3-D camera. One of these is described in the above-mentioned U.S. Pat. No. 4,575,805. The basic approach is to take four images at different positions of the line pattern (ruling) with respect to the object. Between these images the line pattern is shifted by an amount corresponding to a phase shift of 90° with respect to the periodicity of the pattern. These images are then used for calculating the height profile. This is done by first taking the differences between the image for 0° phase shift and the image for 180° phase shift, and between the 90° and 270° images, respectively. The first difference is called the 0°–180° image, the second the 90°–270° image. For any given pixel, the intensity values of these difference images can be shown to correspond to the real and imaginary parts, respectively, of a complex number. The complex phase of this number is then proportional to the height value of the corresponding pixel with respect to a fixed reference height.

A slightly different technique is proposed in the above-mentioned article in the journal "Technisches Messen: Sensoren, Geräte, Systeme". There, the line pattern is moved continuously across the object while the images are taken. The detector integrates the actual intensity in each pixel over a certain time span, e.g. 1/30 sec. with an inter-line CCD which is operated according to the NTSC norm. If the velocity of the moving pattern is chosen in such a way that during the integration period of four images the pattern is shifted exactly by one period (360°), and if four continuous images are acquired, the height profile can be calculated in a similar manner as for four images with a static, phase-shifted pattern.

The line pattern (reference pattern) can be produced, e.g., by a mechanical grating or by an LCD arrangement in the projected beam. With a mechanical grating, the movement of the line pattern can be achieved by moving the grating, e.g., via a coil-and-plunger construction or via a piezo actuator. If the line pattern is produced by an LCD element, the movement can be generated electronically by applying appropriate electronic signals to it.

For a given period of the reference pattern, there is an unambiguous range, i.e., the range in which the height difference between two object points can be unambiguously recorded, according to the following formula:

Unambiguous range=period of the reference pattern divided by the tangent of the angle which the projection optical path and the observation optical path make with one another.

Limited by electrical noise and other effects, the achievable measurement accuracy is always some fraction of the unambiguous range (typically 1/100). Consequently, for a large period the unambiguous range is large, although the height difference between two object points cannot be recorded so accurately. For a small period, the unambiguous range is small but the height difference between two object points can be recorded with great accuracy.

Since it is desirable to be able to record even large height differences between two object points unambiguously and accurately, a 3-D camera has been proposed in DE 90 13 454 U1 in which means for producing a first reference pattern and a second reference pattern on the object of interest are present in the projection optical path. By projecting reference patterns with preferentially different periods onto the object of interest, a substantially larger height difference between two object points can be recorded unambiguously compared with the use of only one reference pattern.

A disadvantage with this that either superposition of the first grating on the second is necessary, with the result that poorer measurement accuracy is achieved on the whole, or a long recording time is necessary. On the whole, the design outlay is very high.

Even in the case of unfavourable surface structures, in order to make measurement of the surface structure possible here, further means for producing a further group of light beams are proposed, which can be guided onto the object of interest from a second direction, different from the first, via a further projection optical path. As a result, the surface structure can be illuminated from different directions, it being proposed that a means for producing a reference pattern be arranged in each projection optical path.

A disadvantage with this is that the equipment outlay is large precisely for manually operated 3-D cameras, and a device which is easy to handle can therefore only be produced with difficulty.

This disadvantage also arises with WO 98/11 403 A1, which discloses a process and a device for the three-dimensional measurement of objects by optical recording, projected patterns and triangulation calculations, in which the projection unit for the pattern and the recording unit are constructed separately from one another and can be positioned or introduced in the course of the measurement process independently of one another.

SUMMARY OF THE INVENTION

An object of the invention is consequently to achieve unambiguous measurements when there are large height differences, without thereby reducing the measurement accuracy and nevertheless keeping the equipment outlay low.

In light of the aforementioned object, the invention provides a 3-D camera that comprises a light source to illuminate the object, where a light beam emitted from said light source defines a projection optical path. The camera also includes an image sensor for receiving light back-scattered by the object, the back-scattered light emanating from the object defining an observation optical path. A grating or LCD for producing a reference pattern projected onto the object of interest is arranged in the projection optical path. A diaphragm is disposed in one of the paths for altering a triangulation angle, which is defined by the angle between a centroid beam of the projection optical path and a centroid beam of the observation optical path.

The invention also provides a method for recording surface structures on an object of interest by means of triangulation, for dental purposes. In one step, at least two 3-D measurements of the object of interest are obtained in close chronological succession. In addition, the triangulation angle between the centroid beam of the projection optical path and the centroid beam of the observation optical path is altered between two of the measurements.

Further features and advantages of the invention, as well as the structure and operation of various embodiments of the invention, are described in detail below with reference to the accompanying drawings.

BRIEF DESCRIPTION OF THE DRAWINGS

The accompanying drawings, which are incorporated herein and form part of the specification, illustrate the present invention and, together with the description, further serve to explain the principles of the invention and to enable a person skilled in the pertinent art to make and use the invention.

DETAILED DESCRIPTION OF THE PREFERRED EMBODIMENTS

Figure 1:
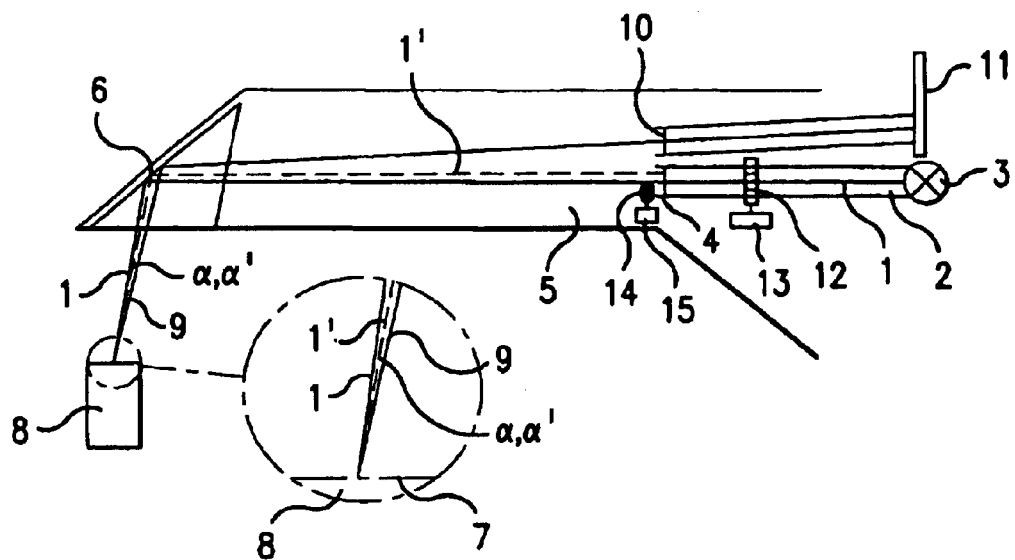
FIG. 1 shows a basic optical path of the 3-D camera.

The present invention provides a 3-D camera for recording surface structures on an object of interest by means of triangulation, in particular for dental purposes, having means for producing a group of light beams in order to illuminate the object of interest via a projection optical path, an image sensor for receiving light back-scattered by the object of interest via an observation optical path, and having means in the projection optical path for producing a pattern projected onto the object of interest.

According to the invention, the 3-D camera contains means in the projection optical path and/or the observation optical path for altering the triangulation angle, which is defined by the angle between the centroid beam of the projection optical path and the centroid beam of the observation optical path.

The means for altering the triangulation angle bring about an alteration to the centroid beam of the projection and/or observation optical path. By providing these means, unambiguous measurements can be obtained when there are large height differences while maintaining a compact structure.

According to one embodiment, the means for altering the triangulation angle is a diaphragm whose shape and/or position can be altered. By opening or closing the diaphragm, the centroid beam can be shifted, an asymmetric diaphragm being required to that end.

According to another embodiment, the means for altering the triangulation angle is a shading or shadow plate which is introduced into the projection and/or observation optical path, in particular in the form of an element of any shape or size, such as a plate, slide, or vein driven by a solenoid.

In another embodiment, a diaphragm is employed which has liquid crystals whose optical transmission can be altered.

It is furthermore advantageous to alter both the course of the centroid beam of the projection optical path and the course of the centroid beam of the observation optical path, in order more greatly to affect the difference in the triangulation angle.

An acceptable angle for the triangulation angle is in particular from 3° to 15°, the triangulation angle being alterable by from 3 to 50%.

Another embodiment of the invention provides a method for recording surface structures on an object of interest by means of triangulation, in particular for dental purposes. In the method according to the invention, at least two 3-D measurements of the same object of interest are carried out in close chronological succession, the triangulation angle between the centroid beam of the projection optical path and the centroid beam of the observation optical path being slightly altered between the two measurements. This alteration of the triangulation angle leads to different recordings of the object to be measured, from which the three-dimensional form of the object can be calculated.

Advantageously, the triangulation angle is altered by a factor of between 0.7 and a value less than 1 or by a factor between a value greater than 1 and 1.3. This means that the triangulation angle is reduced to at most 0.7 times its initial value or increased to at most 1.3 times its initial value. In this range, a satisfactory increase in the unambiguous range can be achieved, satisfactory quality of the signals being a precondition. The quality of the signals has to be the better the closer the factor by which the triangulation angle is altered is to 1.

Advantageously, the alteration of the triangulation angle after the first measurement is carried out by shading or opening the projection and/or observation optical path, which shifts the position of the centroid beam, by means of a diaphragm whose shape and/or position can be altered.

The invention will now be described with reference to the Figures. In FIG. 1, a projection optical path 1 is defined by a first group of light beams 2 which can be produced by an optical source or optical means 3. For example, the optical means 3 can include an LED (or other light source) and a lens. The projection optical path 1 is represented by the centroid beam. The term centroid beam is intended to mean the beam which forms the average in relation to the cross-sectional area and intensity of the group of light beams 2. More precisely, this means that the position of the centroid beam in a cross-sectional surface of the group of light beams is obtained by averaging the cross-sectional point coordinates weighted with the respective light intensity at a cross-sectional point. In a group of light beams with uniform intensity and circular form, the centroid beam passes through the centre of the circle.

The group of light beams 2 of the projection optical path 1 passes through a diaphragm 4 into a prism tube 5 from which the group of light beams emerges, after deviation by means of a prism 6, at a predetermined angle with respect to the longitudinal axis of the prism tube 5. The group of light beams emerging from the prism tube 5 via the prism 6, which is represented by the centroid beam, strikes the surface 7 of an object 8 to be measured and is back-scattered there.

The back-scattered light passes along an observation optical path 9. The centroid beam of the observation optical path 9 intersects the surface 7, an angle α referred to as the triangulation angle being included between the projection optical path and the observation optical path. The light back-scattered by the object 8 of interest is again deviated along the observation optical path 9 via the prism 6 and is delivered through the prism tube 5 and a second diaphragm 10 to an image sensor 11. The image sensor 11 converts the received light signals into electrical signals which are delivered to a signal-processing device, known from the documents cited at the start, so as to obtain data from which an image of the surface structure of the object 8 of interest can be created.

A grating 12 can be inserted into the projection optical path which can be moved in a direction perpendicular to the lines of the grating by a piezo actuator 13. In this embodiment, the grating is arranged in the beam in such a way that an image of the grating is projected onto the surface 7, forming a reference pattern on the surface. By activating the piezo actuator 13, the grating is moved, and the reference pattern correspondingly moves across the surface 7. Alternatively, instead of a mechanical grating, an LCD element could be employed for generating a reference pattern.

The optical elements needed to form an image of the objects on the image sensor have not been represented for the sake of simplicity, and likewise the optical elements needed for forming an image of the grating on the object. This structure is also represented and described in the aforementioned journal "Technisches Messen", pages 257, FIG. 6.

An important feature of the present application is the arrangement of means for shifting the centroid beam in the projection and observation optical paths 1 and 9, respectively. As shown in FIG. 1, the diaphragm 4 is to that end designed so that it can be shaded or shadowed in a lower region, so that the centroid beam 1 shifts upwards, represented by the dashed line 1'. Following the projection optical path 1' with a partially shaded diaphragm 4 clearly shows that the triangulation angle α has been reduced, this angle being therefore denoted α' the triangulation angle α has been reduced, this angle being therefore denoted α'.

Shading the diaphragm shifts the centroid beam, and the light signals received by the image sensor 11 are therefore attenuated compared with the light signals measured with the diaphragm open. The precise manner in which the centroid beam is shifted is not of direct importance for the basic principle of the invention. The diaphragm could, however, be shaded for example by means of an element, such as a plate or slide 14 driven by a solenoid coil 15, which to increase reproducibility is moved against a stop. For example, in one embodiment, a thin lamina is fixed to a plunger in a solenoid coil. Alternative embodiments include diaphragms whose shape and/or position can be altered, or pin hole diaphragms controlled by an LCD array. Optimum utilization of the available space is an important factor in the choice of the means to be used for altering the centroid beam. Regardless of their specific embodiment, the shading means are arranged close to the diaphragm 4.

An explanation will be given below of how unambiguous measurement results can be calculated from two recordings with slightly different triangulation angles, even beyond the original unambiguous range of the individual recordings.

Figure 2:
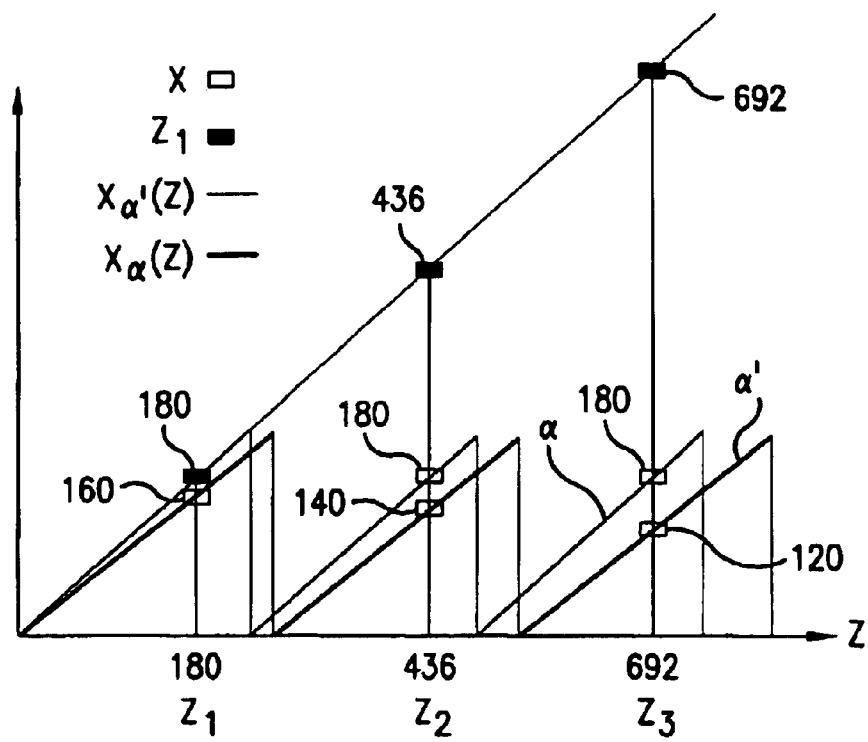
FIG. 2 shows a height profile which is measured.

In FIG. 2, the measured height values $x_\alpha$, $x_\alpha'$ as obtained in the two measurement recordings according to the invention are plotted in a diagram against the true height profile z of the object measured.

The ambiguity of the individual measurement recordings leads in this case to the "sawtooth" shape of the diagram. The period of the "sawtooth" is the unambiguity range (E) of the individual recording. It can be seen that for large values of z, the difference between the measurements $x_\alpha$ and $x_\alpha'$ is large. The difference thus makes it possible to draw conclusions about which unambiguous range (order) the object point lies in. If the order is known, the absolute height value z can be calculated from $x_\alpha$ and $x_\alpha'$ as shown for the heights Z1, Z2 and Z3 in FIG. 2. To that end, only the correct multiple of E is added to the value $x_\alpha$. Through such calculation on the values $x_\alpha$ and $x_\alpha'$ from the individual recordings, the ambiguity of the individual recordings is thus eliminated. The double recording is unambiguous in a multiple range, and to be precise the resulting unambiguous range of the double recording is greater by the factor $\alpha/(\alpha-\alpha')$ than that of the individual recordings as can be understood with a little thought. With the typical values on which the proposition according to the invention is based, an enhancement by a factor of 10 can be obtained.

The measurement accuracy (noise) as given by the first measurement at triangulation value $\alpha$, is not in this case altered since only the fixed value E is added repeatedly to the measurement. This is true even if the quality of the second recording is reduced, for example because of a lower light intensity.

Motion of the camera relative to the object between the two measurement recordings likewise does not affect the measurement accuracy for the same reason, and can at worst have the effect that the wrong multiple of E is added.

The freedom of the double triangulation technique from ambiguities also makes it possible to take absolute measurements of the position which the object to be measured has relative to the camera.

These may also be used, for example, for fine correction of errors in the optical image formation or else of positioning errors by the user.

Although the invention has been described above by reference to certain embodiments of the invention, the invention is not limited the embodiments described above. Modifications and variations of the embodiments described above will occur to those skilled in the art, in light of the above teachings. The scope of the invention is defined with reference to the following claims.

German Patent Application No. 198 29 278.3, filed Jun. 30, 1998, including the specification, the drawings, the claims, and the abstract, upon which this application is based, is incorporated herein by reference in its entirety.

What is claimed is:

1. A 3-D camera for recording surface structures on an object, comprising:
   a light source to illuminate the object, wherein a light beam emitted from said light source defines a projection optical path;
   an image sensor for receiving light back-scattered by the object, the back-scattered light emanating from the object defining an observation optical path;
   a reference pattern projector for producing a pattern projected onto the object; and
   a diaphragm disposed in one of said paths for altering a triangulation angle, which is defined by the angle between a centroid beam of the projection optical path and a centroid beam of the observation optical path.

2. A 3-D camera according to claim 1, further comprising a shading plate insertable into at least one of said paths.

3. A 3-D camera according to claim 2, wherein the shading plate comprises a slide driven by a solenoid.

4. A 3-D camera according to claim 1, wherein said diaphragm comprises liquid crystals whose optical transmission is alterable.

5. A 3-D camera according to claim 1, further comprising a second diaphragm disposed in another of said paths, wherein one of said diaphragms alters a course of the centroid beam of the projection optical path and one of said diaphragms alters a course of the centroid beam of the observation optical path.

6. A 3-D camera according to claim 1, wherein the triangulation angle lies in the range from 3° to 15°.

7. A 3-D camera according to claim 1, wherein the triangulation angle is alterable in an amount from 3 percent (%) to 50%.

8. A 3-D camera according to claim 1 used for dental purposes.

9. A 3-D camera according to claim 1, wherein said reference pattern projector comprises a grating disposed in said light beam to form an image of said grating on a surface of the object.

10. A method for recording surface structures on an object of interest by means of triangulation, for dental purposes, comprising:
    measuring at least two 3-D measurements of the object of interest in close chronological succession; and
    altering the triangulation angle between a centroid beam of the projection optical path and a centroid beam of the observation optical path between two of the at least two measurements;
    wherein the step of measuring comprises measuring with a 3-D camera for recording surface structures on an object which comprises
    a light source to illuminate the object, wherein a light beam emitted from said light source defines a projection optical path;
    an image sensor for receiving light back-scattered by the object, the back-scattered light emanating from the object defining an observation optical path;
    a reference pattern projector for producing a pattern projected onto the object; and
    a diaphragm disposed in one of said paths for altering a triangulation angle, which is defined by the angle between a centroid beam of the projection optical path and a centroid beam of the observation optical path.

11. A method according to claim 10, comprising:
    reducing the triangulation angle to at most 0.7 times its initial value.

12. A method according to claim 10, comprising:
    increasing the triangulation angle to at most 1.3 times its initial value.

13. A method according to claim 10, wherein altering the triangulation angle comprises:

shifting the position of the centroid beam by means of a diaphragm whose shape and position are alterable.

14. A method according to claim 13, wherein shifting the position of the centroid beam comprises adjusting a diaphragm in the projection optical path after a first measurement of the at least two measurements.

15. A method according to claim 13, wherein shifting the position of the centroid beam comprises adjusting a diaphragm in the observation optical path after a first measurement of the at least two measurements.

16. A method according to claim 15, further comprising adjusting a diaphragm in the projection optical path after a first measurement of the at least two measurements.

17. A 3-D camera for recording surface structures on an object of interest by means of triangulation, comprising:
   means for producing one or more light beams to illuminate the object of interest via a projection optical path;
   an image sensor for receiving light back-scattered by the object of interest via an observation optical path;
   means in the projection optical path for producing a pattern projected onto the object of interest; and
   means in the projection optical path or the observation optical path for altering a triangulation angle, which is defined by the angle between a centroid beam of the projection optical path and a centroid beam of the observation optical path.

18. A 3-D camera according to claim 17, wherein the means for altering the triangulation angle comprises a diaphragm having an alterable shape and position and through which a course of the centroid beam can be altered.

19. A 3-D camera according to claim 18, wherein the diaphragm comprises liquid crystals whose optical transmission can be altered.

20. A 3-D camera according to claim 17, wherein the means for altering the triangulation angle comprises a shading plate insertable into the projection path and/or the observation optical path.

21. A 3-D camera according to claim 20, wherein the shading plate comprises a slide driven by a solenoid.

22. A 3-D camera according to claim 17, wherein a course of the centroid beam of the projection optical path and a course of the centroid beam of the observation optical path are alterable by the means for altering the triangulation angle.

23. A 3-D camera according to claim 17, wherein the triangulation angle lies in the range from 3 degrees (°) to 15°.

24. A 3-D camera according to claim 17, wherein the triangulation angle is alterable in an amount from 3 percent (%) to 50%.

25. A 3-D camera according to claim 17 used for dental purposes.

* * * * *